(12) United States Patent
Kim et al.

(10) Patent No.: US 6,992,161 B1
(45) Date of Patent: Jan. 31, 2006

(54) WATER-SOLUBLE OR WATER-DISPERSIBLE GRAFT POLYMERS, THEIR PREPARATION AND USE

(75) Inventors: Son Nguyen Kim, Hemsbach (DE); Axel Sanner, Frankenthal (DE); Peter Hössel, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 995 days.

(21) Appl. No.: 08/743,071

(22) Filed: Nov. 4, 1996

(30) Foreign Application Priority Data

Nov. 8, 1995 (DE) ................................ 195 41 658

(51) Int. Cl.
*C08H 1/00* (2006.01)
*C08G 18/32* (2006.01)
*C08G 18/38* (2006.01)
*C08J 3/03* (2006.01)
*A61K 7/06* (2006.01)

(52) U.S. Cl. .................. 527/204; 424/70.1; 424/70.11; 424/70.12; 424/70.122; 424/70.14; 424/70.17; 435/174; 435/180; 524/591; 524/839; 524/840; 525/54.1; 525/453; 528/28; 528/60; 528/61; 528/71; 528/80

(58) Field of Classification Search ............... 424/70.1, 424/70.11, 70.12, 70.122, 70.14, 70.17; 524/591, 524/839, 840; 525/54.1, 453; 527/204; 528/28, 60, 61, 80, 71; 435/174, 180
See application file for complete search history.

(56) References Cited

U.S. PATENT DOCUMENTS

| | | | |
|---|---|---|---|
| 3,412,054 A | 11/1968 | Milligan et al. ............ 524/571 |
| 3,523,998 A | 8/1970 | Feinstone et al. ............. 424/78 |
| 3,658,939 A | 4/1972 | Carpenter et al. ............ 528/83 |
| 3,672,955 A * | 6/1972 | Stanley ........................ 435/177 |
| 3,734,874 A | 5/1973 | Kibler et al. ................ 524/603 |
| 3,873,478 A | 3/1975 | Comte et al. ................ 527/101 |
| 3,929,574 A * | 12/1975 | Wood et al. .................. 435/43 |
| 3,943,252 A | 3/1976 | Schroer et al. ............. 428/262 |
| 4,094,744 A * | 6/1978 | Hartdegen et al. .......... 435/182 |
| 4,150,216 A | 4/1979 | Quack et al. ................ 528/290 |
| 4,179,420 A | 12/1979 | Laganis ....................... 524/518 |
| 4,195,127 A * | 3/1980 | Hartdegen et al. .......... 435/174 |
| 4,237,229 A * | 12/1980 | Hartdegen et al. .......... 435/182 |
| 4,300,580 A | 11/1981 | O'Neill et al. .................. 132/7 |
| 4,743,673 A | 5/1988 | Johnston et al. ............... 528/60 |
| 5,362,486 A * | 11/1994 | Nandagiri et al. ............ 424/71 |

FOREIGN PATENT DOCUMENTS

| | | |
|---|---|---|
| DE | 42 25 045 | 7/1992 |
| DE | 42 41 118 | 12/1992 |
| EP | 619 111 | 10/1994 |
| GB | 1128568 | 9/1968 |
| WO | 89/07118 | 8/1989 |

* cited by examiner

*Primary Examiner*—Rabon Sergent
(74) *Attorney, Agent, or Firm*—Novak Druce & Quigg

(57) ABSTRACT

Cationic polyurethanes and polyureas formed from
(a) at least one diisocyanate or reaction product thereof with one or more compounds containing two or more active hydrogen atoms per molecule, and
(b) at least one diol, primary or secondary amino alcohol, primary or secondary diamine or primary or secondary triamine each with one or more tertiary, quaternary or protonated tertiary amine nitrogen atoms
and having a glass transition temperature of at least 25° C. and an amine number of from 50 to 200, based on the non-quaternized or -protonated compounds, or other salts of these polyurethanes and polyureas, are useful as ingredients of cosmetic and pharmaceutical preparations.

13 Claims, No Drawings

WATER-SOLUBLE OR WATER-DISPERSIBLE GRAFT POLYMERS, THEIR PREPARATION AND USE

The present invention relates to water-soluble or water-dispersible graft polymers, to their preparation and to their use in cosmetology.

Water-soluble or water-dispersible polymers, for example polyesters, polyamides or polyurethanes, are increasingly gaining importance owing to their low viscosity. For instance, water-soluble polyurethanes are known which comprise carboxyl-containing diols in copolymerized form, these being disclosed in U.S. Pat. No. 3,412,054 and 3,658,939. They are used as an adhesive and coating composition and in printing inks. Water-dispersible polyurethanes containing sulfonate and/or carboxylate groups are known from DE-A 15 70 615. They are used, for example, for the coating and for the impregnation of textiles, leather, paper, wood and metals. Patent documents U.S. Pat. No. 4,300,580, U.S. Pat. No. 3,734,874, DE-A 26 33 418 and WO-A 89/07118 disclose polyesters which contain $NaSO_3$ groups, have a main chain built up by condensation reaction, and can be broken down into shorter segments by hydrolysis of the ester groups.

It is additionally known that maleic anhydride and trimellitic anhydride can be used to prepare water-soluble esters. The anhydride moiety provides carboxyl groups which are converted into carboxylate groups by neutralization with amines, metal hydroxides and metal carbonates, thereby effecting solubility in water. From DE-A 26 37 167 and U.S. Pat. No. 3,523,998 it is known that polycarboxylic acids and their anhydrides, as polymer components, can also make a contribution to rendering polyesters soluble in water. DE-A 21 44 878 describes polyurethanes which are reaction products of digested casein, water-dispersible polyurethanes and formaldehyde. The polyurethane component employed, inter alia, is a latex obtainable by reacting a polyurethane prepolymer with a sodium taurine solution. The latex possesses a relatively low molecular weight and has a low content of ionogenic or ionic groups, since it comprises no ionogenic or ionic groups other than the sulfonate groups from the taurine. Consequently, a film obtained from the latex is not soluble in water without dispersants. The resulting latex is then reacted with casein and formaldenyde to form the abovementioned reaction product. DE 22 61 056 describes polymers formed by reacting an alcohol-functional polymer with a protein and with an isocyanate.

These highly crosslinked polymers are not water-soluble or dispersible in water and are therefore suitable as leather coating compositions and for the production of soles.

However, no cosmetic use of such polymers has hitherto been described.

In cosmetology, film former polymers are used for setting, shaping and improving the structure of hair. Hair treatment compositions generally comprise a solution of the film former in an alcohol or in a mixture of alcohol and water.

U.S. Pat. No. 4,743,673 describes hydrophilic polyurethane polymers having carboxyl groups in the polymer backbone. These polyurethanes are synthesized from a polyol component, which may be an alkylene glycol, a polyoxyalkylene glycol or a linear polyesterdiol, from a carboxylic ester component having hydroxyl or amino groups, and from an organic isocyanate or isocyanate precursor. The polyurethane therefore comprises ester groups, attached to the polymer backbone, which are subsequently hydrolyzed by heating under reflux with a strong base, such as sodium hydroxide or potassium hydroxide, for from 30 to 60 minutes. Following conversion of the carboxylate groups to the acid form and neutralization with ammonia, a film is obtained from the solution. This film is no longer soluble in water but can only be dissolved in lower aliphatic alcohols and other solvents. Owing to the treatment with the strong base under reflux conditions, especially when a polyesterdiol is used as polyol component, there is hydrolysis not only of the ester groups of the carboxylic ester component but also of the ester groups present in the polyurethane chain. The polyurethane chain is therefore cleaved, resulting in a drastic decrease in the molecular weight of the polyurethanes. Admittedly, use of the polyurethanes in hair sprays is mentioned; however, the films obtained with these polyurethanes are unusable in practice for hair cosmetology since they are either insoluble in water or have too low a molecular weight and, consequently, an inadequate setting effect.

DE-A 42 25 045 describes the use of water-soluble or water-dispersible, anionic polyurethanes as hairsetting compositions. These polyurethanes are synthesized from
a) at least one compound containing two or more active hydrogen atoms per molecule,
b) at least on diol containing acid groups or salt groups, and
c) at least one diisocyanate.

They possess a glass transition temperature of at least 15° C. and acid numbers of from 12 to 150. As component a) preference is given to the use of polyethylene glycol, neopentylglycol and polyesterols. Preferred components b) are dimethylolpropanoic acid, a condensation product of pyromellitic dianhydride and neopentylglycol, and a condensation product of 5-sodium-sulfonato-isophthalic acid with neopentylglycol.

DE-A 42 41 118 describes the use of cationic polyurethanes and polyureas as auxiliaries in cosmetic and pharmaceutical preparations. They are used in particular as film formers in hairsetting compositions, and are synthesized from
a) at least one diisocyanate which can have already been reacted beforehand with one or more compounds containing two or more active hydrogen atoms per molecule, and
b) at least one diol, primary or secondary amino alcohol, primary or secondary diamine or primary or secondary triamine having one or more tertiary, quaternary or protonated tertiary amine nitrogen atoms.

The polymers have a glass transition temperature of at least 25° C. and an amine number of from 50 to 200, based on the nonquaternized or protonated compounds.

EP-A 619 111 describes the use of polyurethanes having carboxylate groups in hairsetting compositions. To provide the carboxylate groups, these polyurethanes contain a compound of the formula

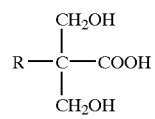

where R is hydrogen or $C_1$–$C_{20}$-alkyl. Some at least of the carboxyl groups are neutralized with an organic or inorganic base in order to provide the number of carboxylate groups required to render the polyurethane soluble in water or in a mixture of water and a polar organic solvent.

Hairsetting compositions are gen rally applied to the hair by spraying in the form of aqueous-alcoholic solutions.

After the solvent has evaporated, the hair is held in the desired shape at the points of mutual contact of the remaining polymer. The polymers should be sufficiently hydrophilic that they can be washed out of the hair but should also be hydrophobic, so that hair treated with the polymers retains it shape, and so that the individual hairs do not stick to one another, even under conditions of high atmospheric humidity. To maximize the hairsetting effect it is also desirable to use polymers of relatively high molecular weight (K value>25) and relatively high glass transition temperature (at least 15° C.). Polymers meeting these requirements, however, are of low hydrophilicity, with the consequence that they are relatively difficult to wash out and can also be used only in the form of alcohol-rich formulations.

When formulating hairsetting compositions, a further consideration is that a reduction in the content of alcohol and propellant is necessary owing to the environmental provisions regarding checks on the emission of volatile organic compounds (VOCs) into the atmosphere.

These contradictory requirements are met only in part by the polymers described in the abovementioned publications. For instance, on the one hand the polymers described in DE-A 42 25 045, DE-A 42 41 118 and EP-A 619 111 do have the desired setting effect owing to their high molecular weight. On the other hand, however, they cannot be washed out sufficiently and can only be used in formulations with a VOC content of more than 80%. The polymers described in U.S. Pat. No. 4,743,673, in turn, are either insoluble in water, and therefore cannot be washed out, or are of such a low molecular weight that they do not have the requisite setting effect.

It is therefore an object of the present invention to provide hair treatment compositions which on the one hand can be used as hairsetting compositions but which on the other hand also possess enhanced washing out properties (redispersibility) and good biodegradability. These hair treatment compositions should also have a low VOC content (<60%).

We have found that this object is surprisingly achieved by water-soluble or water-dispersible graft polymers which represent the reaction product of a urethane prepolymer having terminal isocyanate groups with a prot in which contains free amino groups.

The present invention therefore provides water-soluble or water-dispersible graft polymers of A) a water-soluble or -dispersible urethane prepolymer having terminal isocyanate groups and B) a protein containing free amino groups, and the salts thereof.

The protein B) reacts by way of its free amino groups with the terminal isocyanate groups of the urethane prepolymer, so that the protein is attached to the polyurethane by a urea group. Consequently, the novel polyurethanes have terminal radicals derived from the protein.

In order to obtain good dispersibility in water, the ratio of A) to B) is chosen such that the content of NCO equivalents in A) is less than the content of $N_2$ equivalents in B).

Suitable proteins B) are, quite generally, all proteins having free amino side groups. Both pure proteins and mixtures of different proteins can be used. Other suitable candidates are degradation products of proteins, for example partially hydrolyzed proteins. The degradation products can be obtained by enzymatic degradation, for example by means of protease, or by chemical degradation, for example cleaving of the bases or acids.

The proteins B) employed are preferably caseins and their hydrolysis products.

The proteins B) are generally reacted as an aqueous or aqueous-alcoholic solution, with or without the addition of a base, with the polyurethane prepolymer A).

The reaction of the protein solution with the polyurethane prepolymer A) is generally carried out at a pH>7.

For the reaction with A), it is particularly preferred to employ protein solutions which additionally contain a tertiary amine as base, especially triethanolamine, ethyldiethanolamine or diethylethanolamine. The function of the tertiary amine is to neutralize the carboxyl functions of the protein.

Polyurethane prepolymers A) which can b used in accordance with the invention are known; they are polyurethanes containing ionogenic or ionic groups attached to th polymer chain, so that the polyurethanes are soluble or dispersible in water. These groups are preferably carboxylate groups and/or sulfonate groups and/or groups containing nitrogen. Examples of such polymers are described in U.S. Pat. No. 3,475,206 and 3,412,054 and in DE-A 15 80 615. It is preferred, however, to use the polyurethanes described in DE-A 42 25 045, DE-A 42 41 118 and EP-A-619 111. These polymers are detailed below:

1. Water-soluble or -dispersible anionic polyurethanes of
   a) at least one compound containing two or more active hydrogen atoms per molecule,
   b) at least one compound containing two or more active hydrogen atoms and at least one acid group, tertiary amine group or ionogenic or ionic group per molecule, and
   c) at least one diisocyanate,
   and the salts thereof,
   the ratio of NCO equivalent to equivalent of active hydrogen being from 1:1 to 1.2:1 (ie. ratio of c):(a)+b))).

Component a) particularly comprises diols, diamines, polyester-diols, polyetherdiols or mixtures thereof having a number-average molecular weight of in each case up to 3000, it being possible for up to 3 mol % of the abovementioned compounds to be replaced by triols or triamines.

Examples of diols which can be used are ethylene glycol, propylene glycol, butylene glycol, neopentylglycol, polyetherols, such as polyethylene glycols having molecular weights of up to 3000, block copolymers of ethylene oxide and propylene oxide having number-average molecular weights of up to 3000, or block copolymers of ethylene oxide, propylene oxide and butylene oxide which contain these alkylene oxide units, in copolymerized form, either randomly distributed or in the form of blocks. Preference is given to ethylene glycol, neopentylglycol, di-, tri-, tetra-, penta- or hexaethylene glycol. Other diols which can be used are poly(α-hydroxycarboxylic acid)diols of the formula

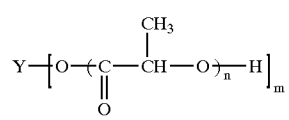

in which Y is the radical of a divalent to tetravalent alcohol, n is from 1 to 50 and m is from 1 to 4 and of the formula

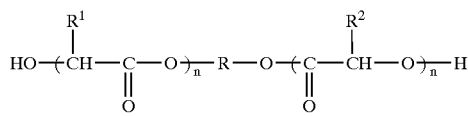

in which $R^1$ and $R^2$ are H, $C_1$–$C_5$-alkyl or aryl (preferably phenyl), R is the radical of a diol ($C_2$–$C_8$-alkylene radical) and n and m are from 1 to 30.

Other compounds which can be used as component a) are silicone compounds of the formula

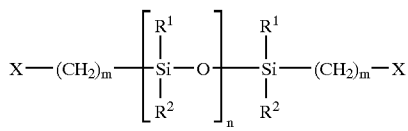

in which $R^1$ and $R^2$ are identical or different and are $C_1$–$C_4$-alkyl, benzyl or phenyl, preferably methyl,
the radicals X, which can be identical or different, are OH or $NH_2$,
m is from 2 to 10, and
n is from 3 to 50.

These silicone compounds can be employed in a quantity of up to 50% by weight, based on the overall weight of components a) and b).

Component b) particularly comprises dimethylolpropionic acid or compounds of the formula

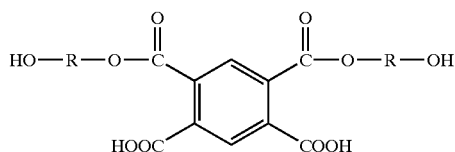

and/or

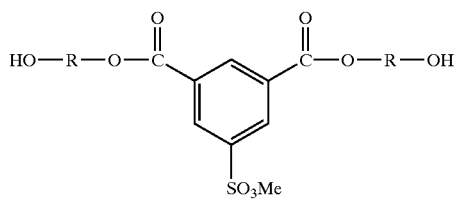

in which R is at each occurrence a $C_2$–$C_{18}$-alkylene group and Me is Na or K.

Component c) is in particular hexamethylene diisocyanate, isophorone diisocyanate and/or tolylene diisocyanate.

The polyurethane prepolymers A) are obtainable by reacting the compounds of groups a) and b) with the compounds of group c) under an inert gas atmosphere in an inert solvent at from 70 to 130° C. If desired, this reaction can be carried out in the presence of chain extenders in order to prepare polyurethanes of relatively high molecular weight. In this reaction, the components are employed in quantities such that the ratio of NCO equivalent to OH equivalent is more than 1 and can be up to 1.2. The ratio is preferably in the range from 1.02 to 1.12. The acid number of the polyurethanes is determined by the composition and concentration of the compounds of component b) in the mixture of components a)+b). The polyurethanes have Fikentscher K values (determined in 0.1% strength by weight solutions in N-methylpyrrolidone at 25° C. and a pH of 7) of from 15 to 100, preferably from 20 to 50.

These polymers and their preparation are described in more detail in DE-A-42 25 045, to which reference is hereby made.

2. Water-soluble or -dispersible, cationic polyurethanes and polyureas of
  a) at least one diisocyanate which can have already been reacted beforehand with one or more compounds containing two or more active hydrogen atoms per molecule, and
  b) at least one diol, primary or secondary amino alcohol, primary or secondary diamine or primary or secondary triamine having one or more tertiary, quaternary or protonated tertiary amine nitrogen atom,
     which have an amine number of from 50 to 200, based on the nonquaternized or protonated compounds, and the salts thereof.

Preferred diisocyanates are those indicated above under 1. Compounds having two or more active hydrogen atoms are diols, amino alcohols, diamines, polyesterols, polyamidediamines and polyetherols. Suitable diols are those indicated above under 1.

Examples of suitable amino alcohols are 2-aminoethanol, 2-(N-methylamino)ethanol, 3-aminopropanol and 4-aminobutanol.

Examples of suitable diamines are ethylenediamine, propylenediamine, 1,4-diaminobutane and 1,6-diaminohexane and α,ω-diamines which can be prepared by amination of polyalkylene oxides with ammonia.

Examples of polyesterols are reaction products of phthalic acid and diethylene glycol, isophthalic acid and 1,4-butanediol, isophthalic acid/adipic acid and 1,6-hexanediol, and of adipic acid and ethylene glycol.

Other compounds having active H atoms which can be used are at least 5 mol % of a poly(lactic ester diol) of the formula

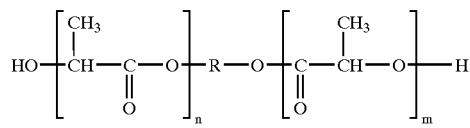

of a poly(ε-caprolactonediol) of the formula II

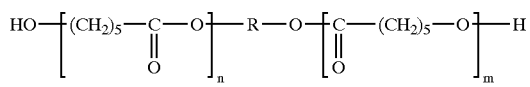

or of a polyamide-diamine of the general formula III

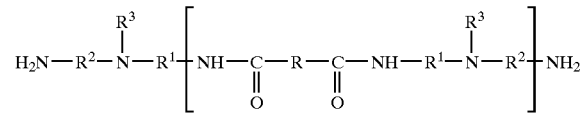

in which
R is $C_2$–$C_8$-alkylene, $C_5$–$C_8$-cycloalkylene or phenylene,
$R^1$ and $R^2$ are $C_2$–$C_8$-alkylene,
$R^3$ is $C_1$–$C_4$-alkyl, phenyl or $C_7$–$C_{10}$-phenylalkyl, and
n and m are each a number from 1 to 30.

Preferred compounds (b) are those of the following:

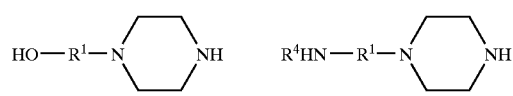

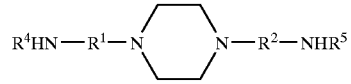

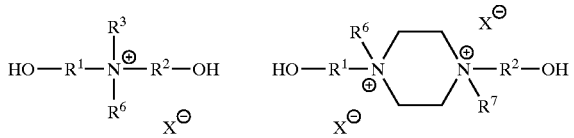

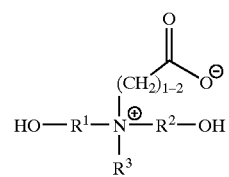

in which
$R^1$ and $R^2$ are $C_2$–$C_8$-alkylene,
$R^3$, $R^6$ and $R^7$ are $C_1$–$C_4$-alkyl, phenyl or $C_7$–$C_{10}$-phenylalkyl,
$R^4$ and $R^5$ are hydrogen or $C_1$–$C_4$-alkyl, and
$X^\ominus$ is chloride, bromide, iodide, $C_1$–$C_4$-alkyl sulfate or half the stoichiometric quantity of sulfate.

The polyurethanes are prepared as described above under 1.

These polymers and their preparation are described in more detail in DE-A-42 41 118, to which, in its entirety, reference is hereby made.

3. Linear polyurethanes containing carboxylate groups, of
   a) a 2,2-hydroxymethyl-substituted carboxylic acid of the formula

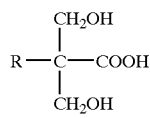

in which R is a hydrogen atom or a $C_1$–$C_{20}$-alkyl group, which is used in a quantity sufficient for from 0.35 to 2.25 milliequivalents of carboxyl groups to be present in the polyurethane per g of polyurethane,
   b) from 10 to 90% by weight, based on the weight of the polyurethane, of one or more organic compounds having not more than two active hydrogen atoms, and
   c) one or more organic diisocyanates.

The carboxyl groups in the polyurethane are finally neutralized, at least in part, with an appropriate base. These polymers and their preparation are described in more detail in EP-A-619 111, to which, in its entirety, reference is hereby made.

It is clear that to prepare the polyurethane prepolymer the diisocyanate must be used in excess in order to obtain a polyurethane prepolymer having terminal isocyanate groups. The polymers according to the invention preferably possess a K value of from 15 to 100, in particular from 20 to 50.

The graft polymers according to the invention are prepared by reacting the polyurethane prepolymer A) with the protein B). Reaction is carried out as known from the prior art for the stopping of polyurethane polymerization with amines. Any isocyanate groups present are finally deactivated by adding amines, for example 2-amino-2-methyl-1-propanol.

The protein is preferably employed in the form of an aqueous or aqueous-alcoholic solution with a pH of more than 7.0 in order to increase the reactivity of the protein. The pH can be established in a customary manner, for example using an alkali metal hydroxide, such as NaOH or KOH, or, preferably, with a tertiary amine, such as triethylamine, a $C_1$–$C_6$-alkyldiethanolamine, for example methyl- or ethyldiethanolamine, or a di-$C_1$–$C_6$-alkylethanolamine.

Th graft polymers of the invention can be used as auxiliaries for the manufacture of textiles, paper and leather and in cosmetology and pharmacy. They are particularly suitable for use in hair cosmetology, where they ar employed as hairsetting compositions. In addition, they can also be used in creams and for coating and binding tablets.

The present invention also provides a hair treatment composition which comprises these novel polyurethanes. In general, the composition comprises the polyurethanes in a quantity of from 0.2 to 20% by weight, based on the overall weight of the composition.

The hair treatment compositions according to the invention are usually in the form of an aqueous dispersion or an aqueous-alcoholic solution. Examples of suitable alcohols are ethanol, propanol, isopropanol, n-butanol, ethylene glycol, propylene glycol, 1,3-butylene glycol or a polyglycol (for example with a molecular weight of 200).

The hair treatment compositions according to the invention additionally comprise, in general, customary cosmetic auxiliaries, for example plasticizers such as glycerol and glycol; silicones; emollients; fragrances; UV absorbers; colorants; thickeners; antistats; combability enhancers; preservatives and foam stabilizers.

When formulated as a hair spray, the compositions according to the invention comprise a sufficient quantity of a propellant, for example a low-boiling hydrocarbon or ether, such as propane, butane, isobutane or dimethyl ether. As propellants it is also possible to use compressed gases, such as nitrogen, air or carbon dioxide. The quantity of propellant is kept as low as possible in order not to cause any unnecessary increase in the VOC content. In general it is not more than 40% by weight, based on the overall weight of the composition.

In addition to the graft polymers according to the invention, the hair treatment compositions can also contain other setting polymers, usually in a quantity of from 0.1 to 10% by weight, based on the overall weight.

The polyurethanes and compositions according to the invention have the advantage that on the one hand they give the hair the desired set and on the other hand that the polymers are more readily able to be washed out (redispersible) than the polymers of the prior art. Moreover, it is possible to produce hair treatment compositions with a VOC content of less than 60% by weight even when these compositions are formulated as a hair spray.

The examples which follow illustrate the invention.

EXAMPLE 1

Polyurethane Preparation:

In a 4-neck flask fitted with stirrer, dropping funnel, thermometer, reflux condenser and a device for working under nitrogen, 0.5 mol of polyesterdiol ($M_w$=1000 g/mol; prepared from isophthalic acid, adipic acid and hexanediol), 0.05 mol of polyethylene glycol (MW 1500) and 1.25 mol of dimethylolpropanoic acid in methyl ethyl ketone were heated to 80° C. and dissolved with stirring. As soon as dissolution was complete, the reaction mixture was cooled to about 50° C. 1.9 mol of isophorone diisocyanate were then added dropwise with stirring, during which there was a rise in the reaction temperature. At an internal temperature of 90° C., the reaction mixture was then stirred until the isocyanate group content of the mixture remained virtually constant. The reaction mixture was then cooled to ambient temperature, at which 116.5 g of casein were added dropwise in the form of a 15% strength aqueous solution of casein/triethanolamine (12:1 w:w). The reaction mixture was then stirred at ambient temperature until isocyanate groups were no longer detectable. Water was subsequently added to the reaction mixture, and the product was neutralized with 2-amino-2-methylpropanol. The methyl ethyl ketone was then distilled off at 40° C. in vacuo to give an aqueous dispersion of the graft polymer (IV, see table), which was used for the tests described in Example 2 below. A dried product can be obtained by spray drying (under vacuum at −80° C.

The other polyurethanes according to the table were prepared analogously.

EXAMPLE 2

Hand Pump Spray Formulation with a VOC Content of 55% By Weight:

| | |
|---|---|
| Graft polymers according to Example 1 (solids content) | 5% by weight |
| Water | 40% by weight |
| Ethanol | 55% by weight |
| Fragrance, surfactant | q.s. |

The hair sprays thus formulated were tested for their setting effect.

Curl Retention=Setting Effect of the Strands of Hair in the Form of Locks at High Atmospheric Humidity (90%):

The curl retention is a measure of the hairsetting effect. It is measured in a model test on locks of hair produced by a customary aqueous perm on hair about 15 cm in length, which was sprayed with a 5% strength by weight (spray) solution of a resin from the table and was neutralized partially (to the extent of 95%) from a distance of 10 cm for 4 seconds. After the suspended locks had been treated for 5 hours in a climatically controlled chamber (25° C., 90% relative atmospheric humidity), the relative deformation (stretching) of the locks, based on the original shape, was determined. A high value denotes a high setting effect; in other words, 100% would denote complete retention of the original form of the suspended locks, while 0% would denote completely stretched hair.

Flexural Strength

Measurement is carried out with 10 different strands of hair of approximately equal weight (2 g) and length (24 cm). The hair is mid-European brown hair. The strands of hair are placed for 1 hour in a 1:1 solution of $EtOH/H_2O$, then shampooed twice with Texapon NSO solution (10% solid) and rinsed with water at 40 C. The wet strands of hair are combed through and dried in air at room temperature. After drying, the strands of hair are weighed and are immersed in a 3% strength ethanolic solution of film former, uniform distribution being ensured by multiple immersion and removal of the strands.

The excess film-former solution is pressed off between thumb and forefinger and the hair is subsequently pressed carefully between filter paper to give a weight increase of from 0.4 to 0.5 g. The strands of hair are then shaped so that they have a circular cross-section. They are dried in a climatically controlled cabinet at 20° C. and 75% relative atmospheric humidity. After 12 hours, the strands are removed from the cabinet and subjected immediately to the hardness measurement. The strands of hair are placed on two cylindrical rolls (diameter 6 mm) which are arranged horizontally to one another at a distance of 9 cm. Exactly in the middle between the two points of contact, a cylindrical roll (diameter 6 mm) is pressed from above onto the strands of hair, with constantly increasing force, until the strands break. The force necessary to achieve breaking is measured by measuring the required mass. After the strand of hair has been broken it is released, as a result of which it stretches again. The force is again increased continually until the strand breaks for a second time.

The setting effect of the individual graft polymers (I to VII) according to the invention is shown in the table.

| Graft polymer* | Poly-(ester-diol) [mol] | PEG E1500 [mol] | DMPA [mol] | H—Si 2111 [mol] | MDEA [mol] | IPDI [mol] | HDI [mol] | Casein [% by weight] | Solubility 5% strength in H$_2$O | Solubility 5% strength in VOC50 | Film redispersibility in H$_2$O:EtOH (1:1) | Setting effect of VOC 55 pump spray curl retention [%] | Setting effect of VOC 55 pump spray flexural strength [cN] |
|---|---|---|---|---|---|---|---|---|---|---|---|---|---|
| (I) | 1 | — | — | — | — | 1.1 | — | 100**) | disp. | disp. | still good | — | — |
| (II) | — | 1 | — | — | — | — | 1.1 | 50 | micro disp. | micro disp. | good | — | — |
| (III) | 1 | 0.1 | 1 | — | — | — | 2.3 | 50 | micro disp. | micro disp. | good | 51 | 312 |
| (IV) | 1 | 0.1 | 2.5 | — | — | 3.8 | — | 10 | micro disp. | soluble | good | 65 | 356 |
| (V) | 1 | 0.1 | 2.5 | — | — | 3.8 | — | 5 | micro disp. | soluble | good | 69 | 517 |
| (VI) | 0.9 | 0.1 | 2.5 | 0.1 | — | 3.8 | — | 5 | micro disp. | soluble | good | 73 | 452 |
| (VII) | 0.5 | 1 | — | — | 0.4 | 2 | — | 10 | disp. | micro disp. | still good | — | — |

*) graft polymer was neutralized after reaction either with 2-amino-2-methylpropanol or with lactic acid
**) % by weight based on the prepolymer overall weight (column 2–8)
Poly(sterdiol) = Polyesterdiol of isophthalic acid, adipic acid and 1,6-hexanediol; M$_w$ = 1000
PEG E1500 = Polyethylene glycol; M$_w$ = 1500
DMPA = 1,1-Dimethylolpropanoic acid
MDEA = N-Methyldiethanolamine
IPDI = Isophorone diisocyanate
HDI = Hexamethylene diisocyanate
H—Si2111 = Siliconediol, M$_w$ = 860, from Th. Goldschmidt AG
Casein alkali-soluble from Merck

We claim:

1. A water-soluble or water-dispersible graft polymer comprising
   A) a water-soluble or -dispersible polyurethane prepolymer having terminal isocyanate groups,
      wherein the polyurethane prepolymer is formed from
      a) at least one compound containing two or more active hydrogen atoms per molecule,
      b) at least one compound other than the compound of (a) containing two or more active hydrogen atoms and at least one acid group, tertiary amine group or ionogenic or ionic group per molecule, and
      c) at least one diisocyanate; and
   B) a protein-containing free amino groups, whereby the protein is attached to the polyurethane by a urea group or a salt of said graft polymer.

2. The graft polymer of claim 1, wherein the ratio of NCO equivalent to equivalent of active hydrogen in A) is from greater than 1:1 to 1.2:1.

3. The graft polymer of claim 1, wherein the ionogenic and/or ionic groups of component b) are carboxylate groups and/or sulfonate groups or nitrogen-containing groups.

4. The graft polymer of claim 1, wherein the compound b) is dimethylolpropionic acid.

5. The graft polymer of claim 1, wherein component a) comprises from 40 to 90% by weight, based on the overall weight of components a) and b), of a polyesterdiol.

6. The graft polymer of claim 1, wherein component a) comprises up to 50% by weight, based on the overall weight of components a) and b), of a silicone compound of the formula

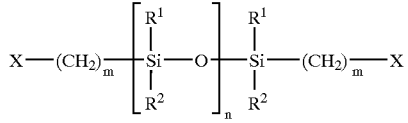

in which
R$^1$ and R$^2$ are identical or different and are C$_1$–C$_4$-alkyl, benzyl or phenyl, the radicals X, which are identical or different, are OH or NH$_2$,
m is from 2 to 10, and
n is from 3 to 50.

7. The graft polymer of claim 1, wherein the proteins (B) are caseins.

8. A hair treatment composition comprising the graft polymer of claim 1.

9. A hair treatment composition comprising
   a) from 0.2 to 20% by weight, based on the overall weight, of a graft polymer as claimed in claim 1 and
   b) from 0.1 to 10% by weight of a further hairsetting polymer other than a).

10. A composition comprising an aqueous solution or dispersion of a graft polymer of
    a) a water-soluble or -dispersible polyurethane prepolymer having terminal isocyanate groups and
    b) an aqueous or aqueous-alcoholic solution of a protein containing free amino groups,
    or salt of the graft polymer, said graft polymer having been formed by reacting the terminal isocyanate groups of the polyurethane prepolymer (A) with a protein (B) containing free amino groups, whereby the protein is attached to the polyurethane by a urea group, and a tertiary amine as a base.

11. The composition of claim 10, wherein the tertiary amine is selected from the group consisting of triethanolamine, ethyldiethanolamine and diethylethanolamine.

12. A hair treatment composition comprising the graft polymer of claim 10.

13. A hair treatment composition comprising
a) from 0.2 to 20% by weight, based on the overall weight, of a composition as claimed in claim 10 and
b) from 0.1 to 10% by weight of further hairsetting polymer other than a).

* * * * *